United States Patent [19]
Ferrand et al.

[11] Patent Number: 5,375,397
[45] Date of Patent: Dec. 27, 1994

[54] CURVE-CONFORMING SENSOR ARRAY PAD AND METHOD OF MEASURING SADDLE PRESSURES ON A HORSE

[76] Inventors: Robert J. Ferrand, 121 Bancroft Rd., Burlingame, Calif. 94010; Joseph A. Sember, III, 2339 Paseo De Cima, Glendale, Calif. 91206

[21] Appl. No.: 196,984

[22] Filed: Feb. 15, 1994

Related U.S. Application Data

[63] Continuation-in-part of Ser. No. 80,805, Jun. 22, 1993, abandoned.

[51] Int. Cl.⁵ .................................................. B68C 1/12
[52] U.S. Cl. .......................................... 54/66; 128/782
[58] Field of Search ...................... 54/65, 66; 128/782

[56]         References Cited
         U.S. PATENT DOCUMENTS

| | | | |
|---|---|---|---|
| 809,276 | 1/1906 | Aulton | 54/65 |
| 823,590 | 6/1906 | Eichhorn | 54/66 |
| 1,357,823 | 11/1920 | Read | 54/66 X |
| 3,872,653 | 3/1975 | Thompson | 54/66 X |
| 4,014,398 | 3/1977 | Gresko | 128/782 X |
| 5,119,618 | 6/1992 | Streck | 54/66 |
| 5,253,656 | 10/1993 | Rincoe et al. | 128/782 |

*Primary Examiner*—Robert P. Swiatek
*Attorney, Agent, or Firm*—Edward B. Anderson

[57] ABSTRACT

A sensor array pad for sensing the pressure distribution under a saddle on the back of a horse includes a membrane made of first and second, identical substantially non-stretchable, flexible membrane portions. The membrane portions have adjacent facing edges that are joined at two spaced-apart tabs. A plurality of sensors are distributed substantially uniformly on the membrane, with each sensor occupying a predetermined surface area. Conductors are mounted on the membrane to extend between the sensors and a position along the perimeter of the associated membrane portion to provide for external connection with monitoring equipment. The membrane portions further each have a pair of slits extending from a mid-region spaced from the respective facing edge outwardly in diverging directions along lines passing outside the predetermined areas of the membrane occupied by the sensors. The slits define an upper section extending generally along the spine of a horse and a side section extending down the side of the horse away from the spine. When placed on the back of a horse with the facing edges extending along the spine, the membrane generally conforms to the back of the horse with the upper and side sections separating by spreading of the slits. The membrane may also be stretchable between the individual sensors. Pressures sensed by the sensors are input to a computer which generates a display of the pressure distribution.

32 Claims, 11 Drawing Sheets

COLUMNS: DATA RETURN

ROWS: SIGNAL SOURCE

CURVE-CONFORMING SENSOR ARRAY PAD AND METHOD OF MEASURING SADDLE PRESSURES ON A HORSE

CROSS REFERENCE TO RELATED APPLICATION

This is a continuation-in,part of copending application Ser. No. 08/080,805 filed Jan. 22, 1993 now abandoned.

BACKGROUND OF THE INVENTION

1. Field of the Invention

This invention relates to measuring saddle pressures on a horse, and in particular, the distribution of pressure measured by a sensor array pad placed between a saddle and horse. The sensor array pad accommodates the compound curvature of the back of a horse by placing an array of sensors on a membrane support that is stretchable between sensors or sets of sensors on sections of the pad, or on a non-stretchable membrane support configured to conform to the compound curved surface.

2. Related Art

For centuries, people have ridden horses and fit a multitude of saddles on them with very little understanding of the effect of the saddle on the horse. Traditionally, saddle fit has been determined by riding the horse and then observing the sweat pattern on the horse's back.

It is expected that a majority of the over 10,000,000 horses in the United States and 3,500,000 in Europe may have sore backs from poorly fitting saddles. Since there is no recognized way to ask a horse how a saddle fits, there is a need for an apparatus that can be used to objectively measure the fit of a saddle on a horse.

Talley, Inc. of Romsey, England developed a pad formed of air cells that are connected to a controller unit via thin, flexible hard plastic tubes. Such a system is very cumbersome. Vistamed of Winnipeg, Canada developed an array using force-sensitive resistors,. A company known as Tekscan of Cambridge, Mass. developed an extensive and dense array using a force-sensitive ink printed on a polyester film.

A disadvantage of such pads, however, is that they are made for use in planar or simple curvature surfaces. When they are applied to a compound curvature surface, such as the back of a horse, they buckle and distort, preventing accurate and consistent determination of the pressures distributed across the surface of interest.

Sensor array pads are known to be used for mapping the pressure between a person and a wheel chair seat or bed surface. These systems include an array pad formed of pressure-responsive sensors distributed on a stretchable, flexible membrane. Signals from the sensors are converted to digital form and fed into a computer that then generates pressure distribution data that can be saved in memory, printed out, or displayed on a monitor.

It has been found that this system provides the necessary pressure mapping over a pad array area corresponding to the area of a wheel chair or bed. The stretchable, flexible membrane is found also to conform to the compound curvatures of a horses back. However, the sensor array size is inappropriate for use in measuring the distribution of pressures for an entire saddle. If it is set on one side of the saddle, it tends to migrate under the saddle. If it is placed over the spine of a horse, the sensors over the spine area are not used because the saddle does not rest on that area of a horse. Further, the membrane is manipulated and tends to become distorted over the spine, stressing the structural integrity of any sensors on the membrane. The sensors produce erroneous signals when not properly sandwiched between the horse and saddle.

Up to now, there has not been an apparatus or method of determining the amount and distribution of pressures between a saddle and a horse, particularly one that accommodates the shape of a horse's back and the structure of a saddle. Nor has there been a system that provides for improvement in the saddle/horse interface, such as by modifying the saddle structure or rider posture to alter the pressure distribution.

SUMMARY OF THE INVENTION

The present invention overcomes these limitations in the known prior art. In particular, the present invention provides a sensor array pad that is configured to conform to the compound curvature of the back of a horse and a method of sensing the pressure distribution under a saddle.

In general, the present invention provides a sensor array pad for sensing the pressure distribution under a saddle on the back of a horse. It includes a plurality of generally planar sensors each having a planar surface and associated edges with each sensor being responsive to a pressure applied on the planar surface for outputting a signal representative of the applied pressure. The plurality of sensors are supported, preferably on a membrane, in a pair of arrays, with each array distributed over an area corresponding to at least a portion of the area of a saddle that is supported on one side of the spine of a horse. One of the arrays is positioned on each side of the spine of a horse. The planar surfaces of the respective sensors conform to the compound curvature of a horse's back when the pad is placed between a saddle and a horse's back.

The pad membranes are preferably either continuous and stretchable, or substantially non-stretchable and flexible and are sized to cover the portion of the back of a horse contacted by a saddle. The non-stretchable membranes are formed identically and have adjacent facing edges that are joined at two spaced-apart locations. The joined membranes are characterized as lying flat when placed on a planar surface. The composite membrane is sized to correspond to the area of a saddle supported on the back of a horse with the facing edges of the individual membranes extending along the spine.

A plurality of sensors are distributed substantially uniformly on the first and second membranes with each ,sensor occupying a predetermined surface area of the associated membrane. Conductors are mounted on the membranes to extend between the sensors and a position along the perimeter of the associated membrane to provide for external connection with monitoring equipment.

The first and second membranes further each have a pair of slits extending from a mid-region spaced from the respective facing edge outwardly in diverging directions along lines passing outside the predetermined areas of the membrane occupied by the sensors. The slits define an upper section of each membrane extending generally along the spine of a horse and a side section extending down the side of the horse away from the spine. When placed on the back of a horse with the facing edges extending along the spine, the membranes generally conform to the back of the horse with the upper and side sections separating by spreading of the slits.

Such a pad is manufactured economically since it is formed of membrane portions that are planar. Further, the use of two identical membrane portions further economizes the manufacture of the pad. By the use of slits and openings at selected locations in the membrane according to the invention, the otherwise planar membrane conforms to the compound curvature of the back of a horse.

The sensors are also preferably distributed in two spaced-apart arrays on the membrane. The center section without sensors aligns with the horse's spine and allows manual manipulation to improve positioning of the arrays and reduce the amount of shear forces on the sensors.

According to another aspect of the invention a method is provided for sensing the pressure under a saddle on the back of a horse. This method includes the steps of (a) positioning between a saddle and the back of a horse a pad having at least one individual pressure-responsive sensor in a fixed position of the pad; (b) positioning a rider in the saddle; (c) sensing from the sensor a signal representative of the pressure applied by the saddle; and (d) determining from the sensed signal the pressure represented by the signal. Such a method allows one to determine the pressure under the saddle to see if it is excessive.

If the pressure is excessive it needs to be reduced in order to provide a better saddle fit or to achieve a better balanced ride. Thus, the method also preferably includes the steps of changing the distribution of pressure applied by the saddle on the horse, sensing from the sensor a modified signal representative of the pressure applied by the saddle on the horse, and determining from the modified sensed signal the pressure represented by the modified signal.

The pad of the invention is also preferably used in the method so that the distribution of pressure corresponding to the two sides of the saddle can be determined. The method thus also may include positioning the sensor array pad, sensing the pressure-representative signal from each sensor, and determining the pressure represented by each sensed signal. This allows a display of the various pressures occurring under the saddle at one time so the variation in pressures under the saddle can be determined. This identifies where changes need to be made overall in order to improve the ride or saddle fit. A templet with an image of the sensor arrays may be placed on the underside of a saddle removed from the horse to identify the locations of sensed pressure readings on the saddle.

These and other features and advantages of the present invention will be apparent from the following detailed description of the preferred embodiment of the invention and the accompanying drawings.

BRIEF DESCRIPTION OF THE DRAWINGS

FIG. I is a side view of a horse carrying on its back a sensor pad assembly made according to the invention.

DETAILED DESCRIPTION OF THE PREFERRED EMBODIMENT

Figure 1:
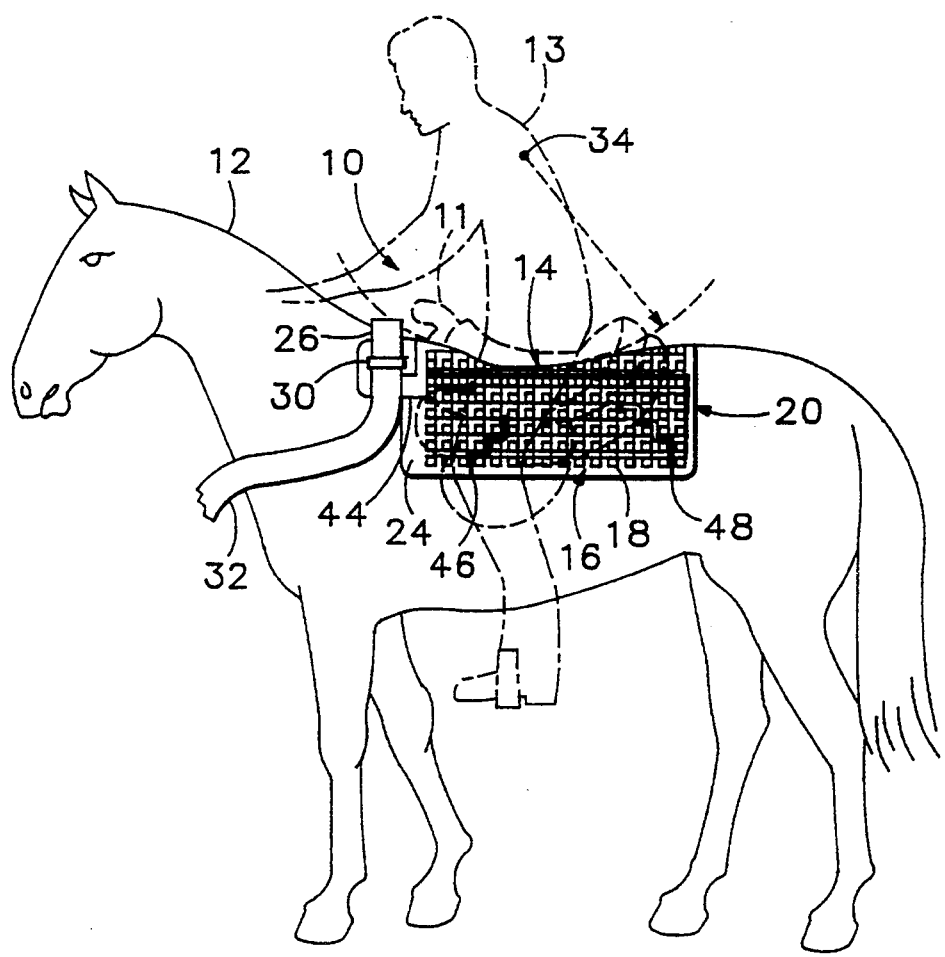
Figure 2:
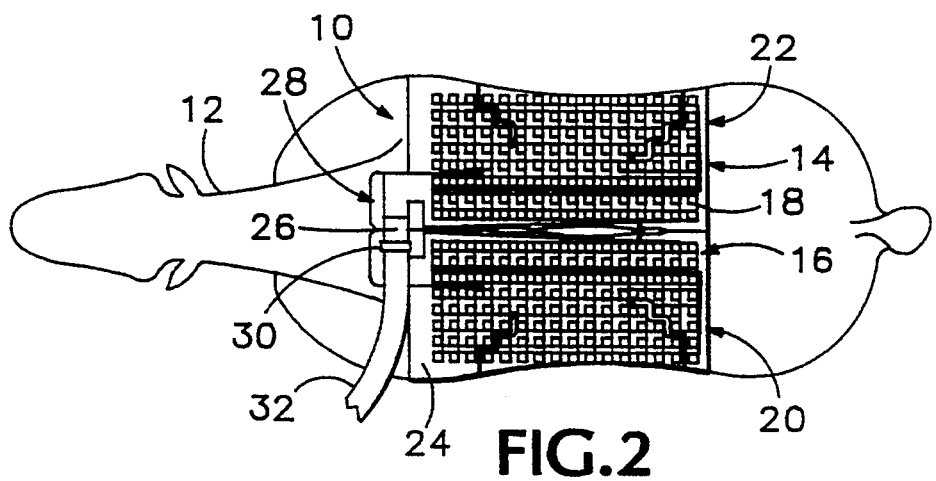
FIG. 2 is a top view of the horse and assembly of FIG. 1.
Figure 3:
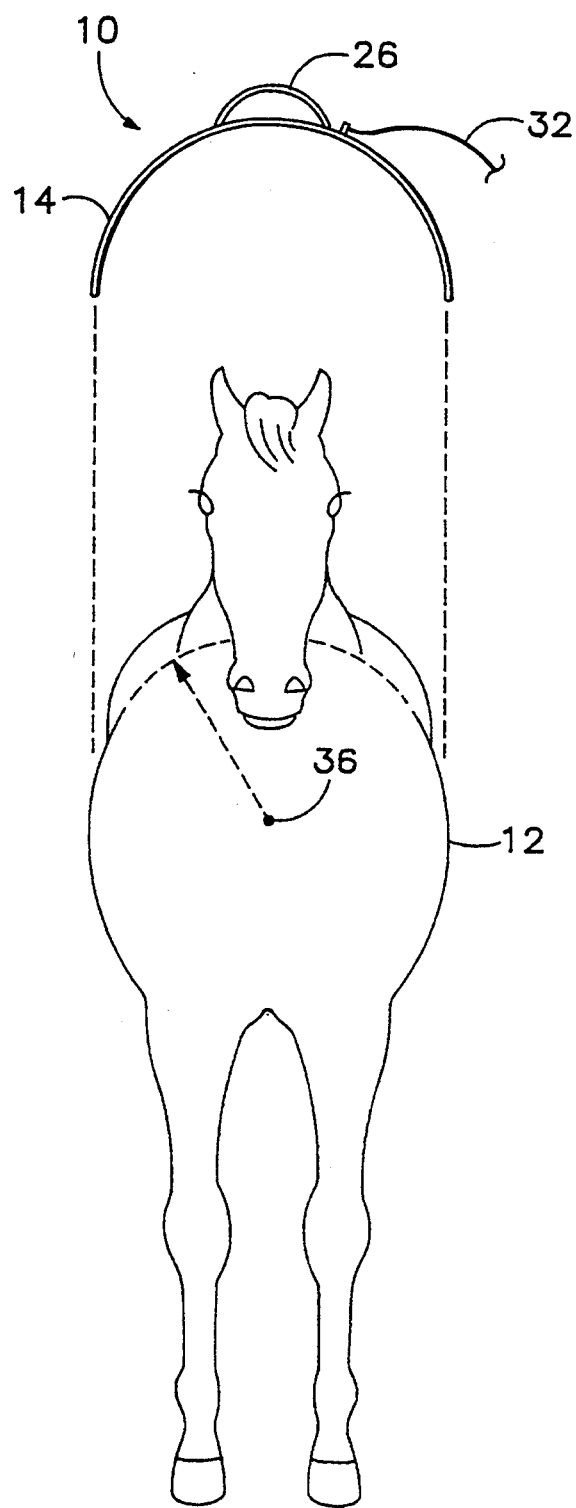
FIG. 3 is a front view of the horse and assembly of FIG. 1.

Referring initially to FIGS. 1–3, an assembly 10 for measuring the pressure distribution on the back of a horse 12 by a saddle 11, shown in dashed lines, ridden by a rider 13, shown in dash-dot lines, includes a first preferred sensor pad 14 having a 16×16 composite array 16 of pressure-sensitive transducers or sensors 18. Pad 14 is preferably 27 inches wide by 27 inches long, is formed of two pad sections 20 and 22 formed by two corresponding sensor arrays 21 and 23 mounted on identical base membranes 24, also referred to as membrane portions forming a composite membrane 25 providing means for supporting the sensors. This pad is big enough to measure the pressure distribution under English, western, and Australian saddles. A 25-conductor service loop 26 of ribbon cable connects a right connector assembly 28 to a left connector assembly 30. A 36-conductor ribbon cable 32, preferably several feet long, or wireless RS-232 interface (not shown), transmits signals between the pad assembly and the computer.

As shown in FIG. 1, the top of the back of the horse curves predominantly about a first axis 34 positioned above and transverse to the line of the horse. The sides of the horse curve predominantly about a second axis 36, shown in FIG. 3, generally corresponding to the longitudinal axis of the body of the horse. Pad 14 conforms without wrinkles to the back of the horse. A longitudinal section 38 of each of .pad sections 20 and 22 conforms to the top of the back that curves about axis 34, and a lateral section 40 that conforms to the sides of the horse that curve about axis 36.

Figure 4:
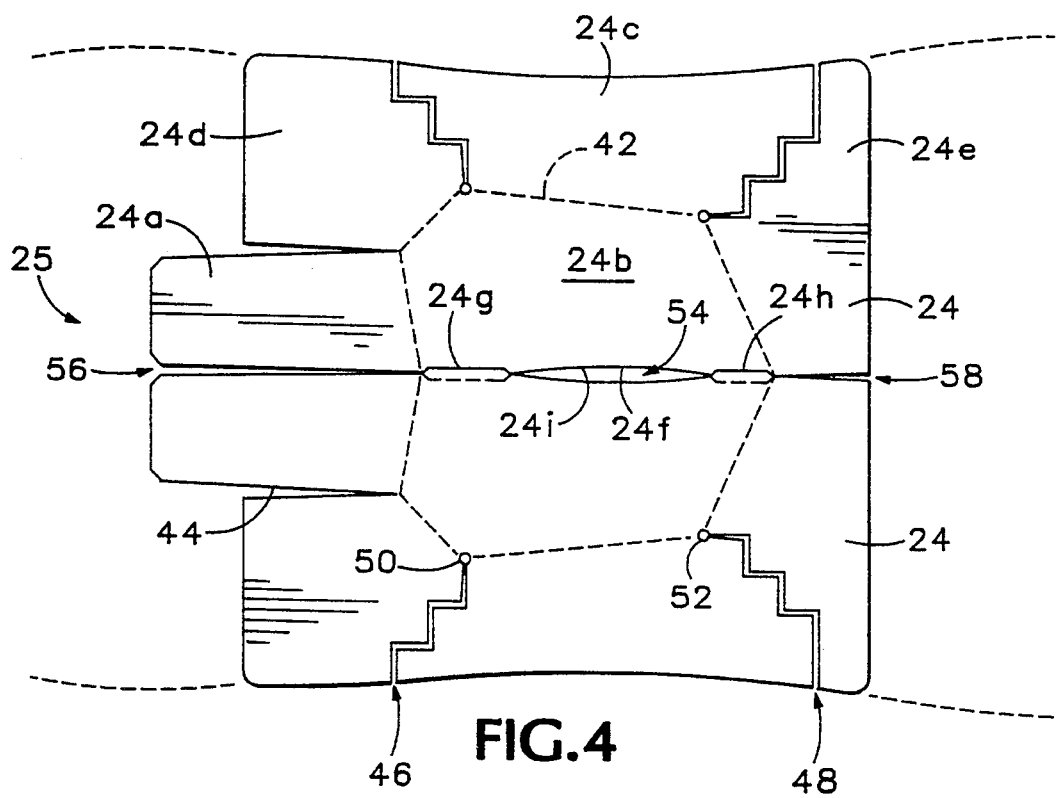
FIG. 4 is an enlarged top view of two joined membranes used in the pad of FIG. 1.

The position of composite membrane 25 on a horse's back is illustrated as a top view in FIG. 4. Membranes 24 are preferably made out of polyester film. This film has little flexibility in the plane of the membrane, but is flexible transverse to the membrane face. In other words, it is flexible but not stretchable during normal use. Each membrane portion has a forward directed tongue 24a, a central section 24b, a lateral section 24c, a front corner section 24d, and a rear corner section 24e. Except for a first or central section 24b, these sections are referred to generally as satellite sections. The other sections may variously be referred to as second, third, and fourth sections. The central section joins the other sections together and holds them in their relative positions. The approximate separation between the sections is represented by the dashed lines, such as line 42, which are equivalent to portions of the membranes which, in this case, integrally hold the respective sections together.

Longitudinal pad section 38 is made up primarily of membrane sections 24a, 24b and 24e. Lateral pad section 40 is made up of section 24c. Front corner section 24d may be considered to be a part of either of these pad sections.

Central section 24b is connected integrally to each of the other sections, but the other sections that are adjacent are separated by an associated slit. For instance, the tongue and front corner section are separated by a slit 44; the front corner and lateral section are separated by a front stair-step slit 46; and the lateral section and rear corner section are separated by a rear stair-step slit 48. Stair-step slits 46 and 48 each terminate in circular openings 50 and 52, respectively. These openings distribute the tension on the tips of the slits to inhibit lengthening of the slits during use.

Each membrane 24 has a side 24f with spaced-apart tabs 24g and 24h. A slightly concave edge 24i extends between the tabs along the outer edge of central section 24b. When the two membranes 24 are placed together as shown, with one upside down and oriented as a mirror image of the other membrane along the two tabs the tabs overlap and are appropriately connected together, such as by a suitable adhesive or by heat welding. The concave edges 24i form an elongate opening 54.

When composite membrane 24 is positioned on a horse, as shown in FIG. 4, each of these slits is slightly flared and at different levels as the membrane portions conform to the horse. Opening 54 actually closes slightly as the two membranes hinge about tabs 24g and 24h, which tabs are also referred to as means for holding the membrane portions together. The resulting front slit 56 between tongues 24a opens as the tongues are positioned on the sides of the withers. The resulting rear slit 58 behind tab 24h slightly separates to allow the rear sections 24e to rest evenly on the horse crup or rump above the front edge of the hips. The tongues 24a lie on the horse shoulders, and the front corner sections 24d lie on the side of the shoulders. Lateral sections 24c lie on the horse sides below and behind the top of the shoulders, and in front of the hips.

Figure 5:
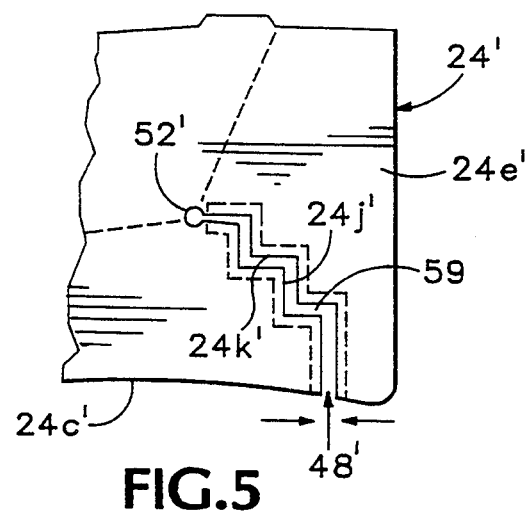
FIG. 5 is a fragmented view similar to FIG. 4 of a portion of an alternative embodiment of a pad membrane.
Figure 6:
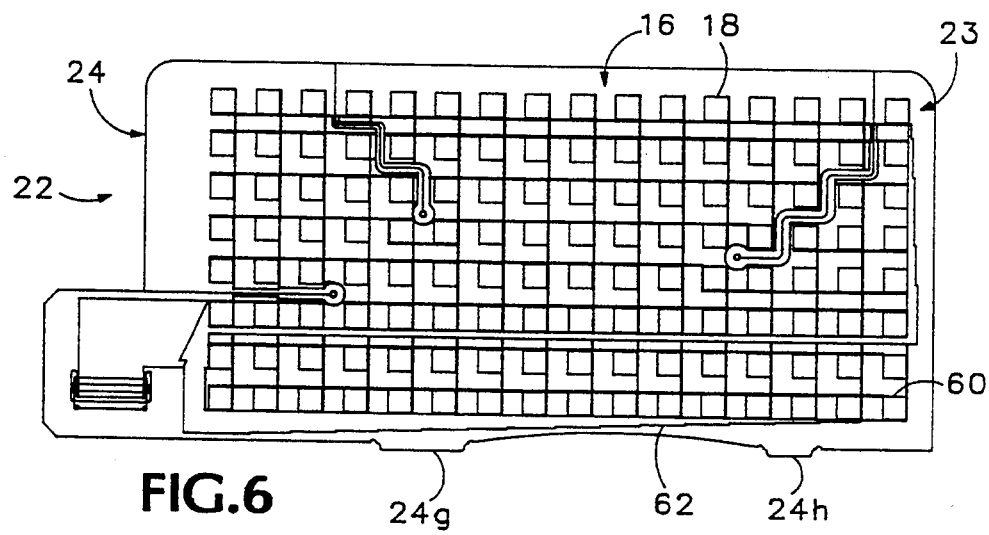
FIG. 6 is a plan view of a portion of the pad of FIG. 1.

Thus, tongue, front and rear slits 44, 46 and 48, respectively, and slits 56 and 58 between joined membranes 24, thus divide the pad into separate sections that correspond to different surface contours on the horse. Each membrane 24 is made from a planar sheet of film that lies flat on a planar surface, as shown in FIGS. 5 and 6. In such a position, the opposing membrane edges along all of the slits except for opening 54 are abutting. When the membrane is placed on the back of a horse as described, the various sections are allowed to conform substantially to the surface of the back without creating any wrinkles. The pressure sensors thereby are permitted to function as designed, providing dependable data.

An alternative embodiment 24' of the membrane or sensor supporting means is shown in fragmented form in FIG. 5. As shown in this figure, sections 24e' and 24c' are separated by a preferably (but not necessarily) enlarged slit 48'. Attached to the lower surface of the membrane is an elastic fabric 59, also referred to as resilient urging means. This fabric, which may be made of a conventional elastic fabric, such as the material known by the proprietary name Lycra, is cut larger than the slit, as shown, and is glued or otherwise suitably attached along the margins of the slit to the membrane. When the membrane is placed on the back of a horse, fabric 59 allows the adjacent edges 24j' and 24k' of sections 24c' and 24e' of the membrane to separate. The other slits of the membrane may be similarly constructed. The elastic fabric urges these adjacent section edges together when they are separated, and generally holds the membrane in tension. This assures that the membrane stays flush with the surface of the horse and that corners of the sections do not fold over. Further, although more expensive to produce, it also holds the sections together when the pad is removed from the horse.

Figure 7:
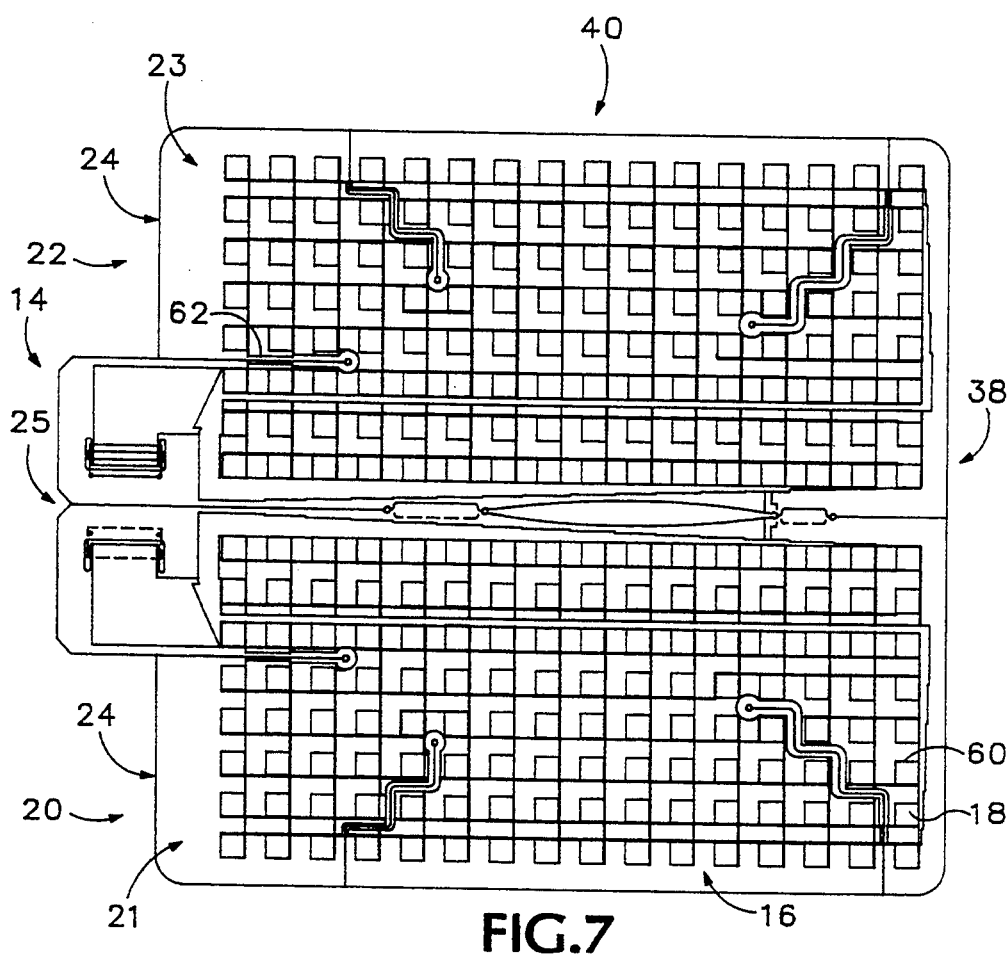
FIG. 7 is a plan view of the pad of FIG. 1.
Figure 8:
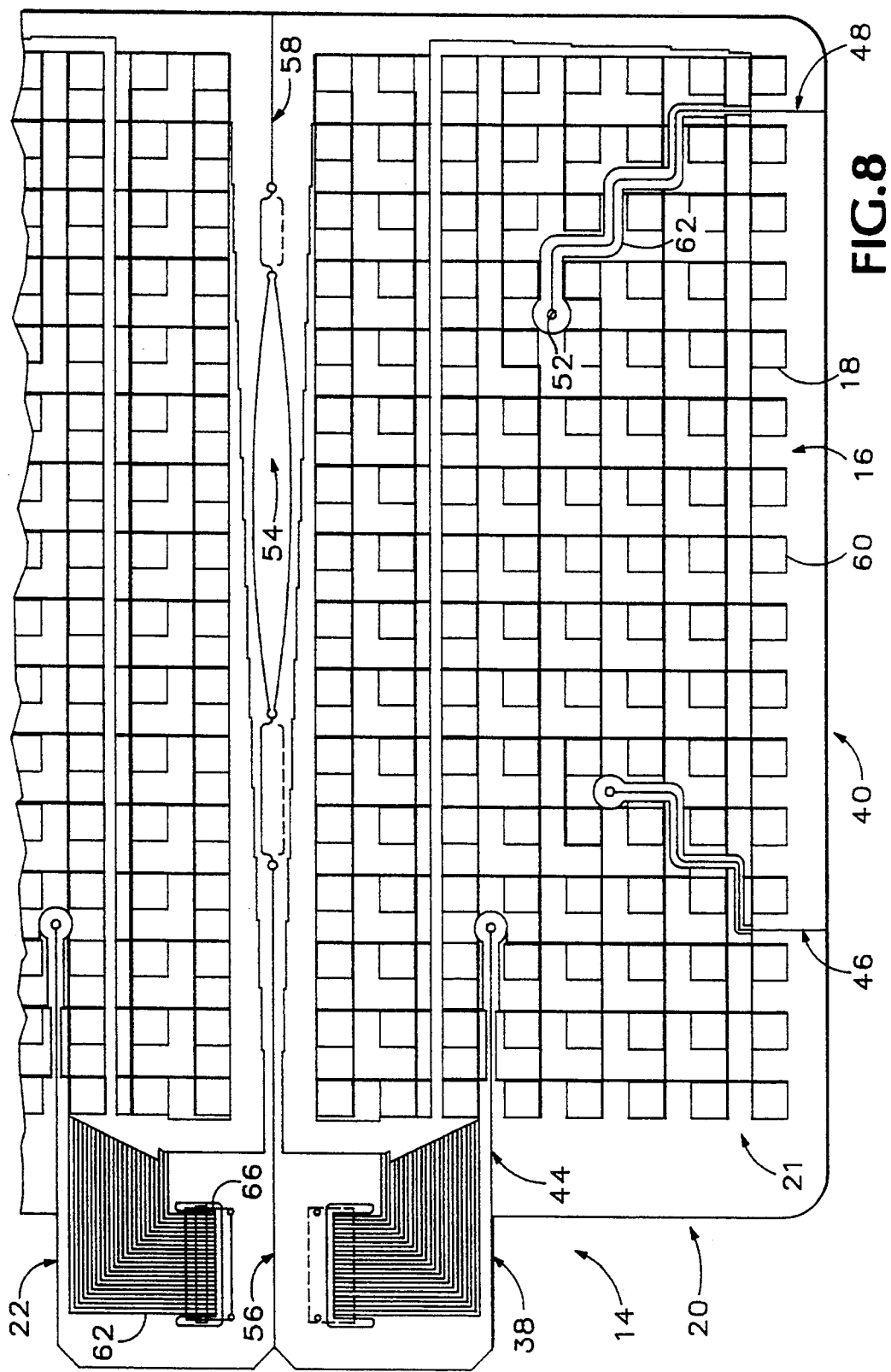
FIG. 8 is an enlarged fragmentary view of the pad of FIG. 7.

As shown particularly in FIGS. 6–10, each membrane 24 has sensors 18 in the form of force-sensitive ink imprinted on them in a regular array, with the area of the sensors represented by rectangles 60, using conventional techniques. A conductor trace 62 is imprinted on the membranes connecting each sensor on the left pad section to connector assembly 30 that includes a circuit board 64, shown in FIGS. 9 and 10, and connecting each sensor on the right pad section to a pin housing 66, forming part of connector assembly 28. FIG. 6 shows a single membrane 24 imprinted with 8×16 array 23 of sensors to form pad portion 22. FIG. 7 shows two such imprinted membrane portions forming pad portions 20 and 22 joined together at tabs 24g and 24h, to form in combination pad 14. These figures show the pad in a planar orientation with the various slits closed, as has been discussed. An enlarged view of a portion of FIG. 7 is shown in FIG. 8

Figure 9:
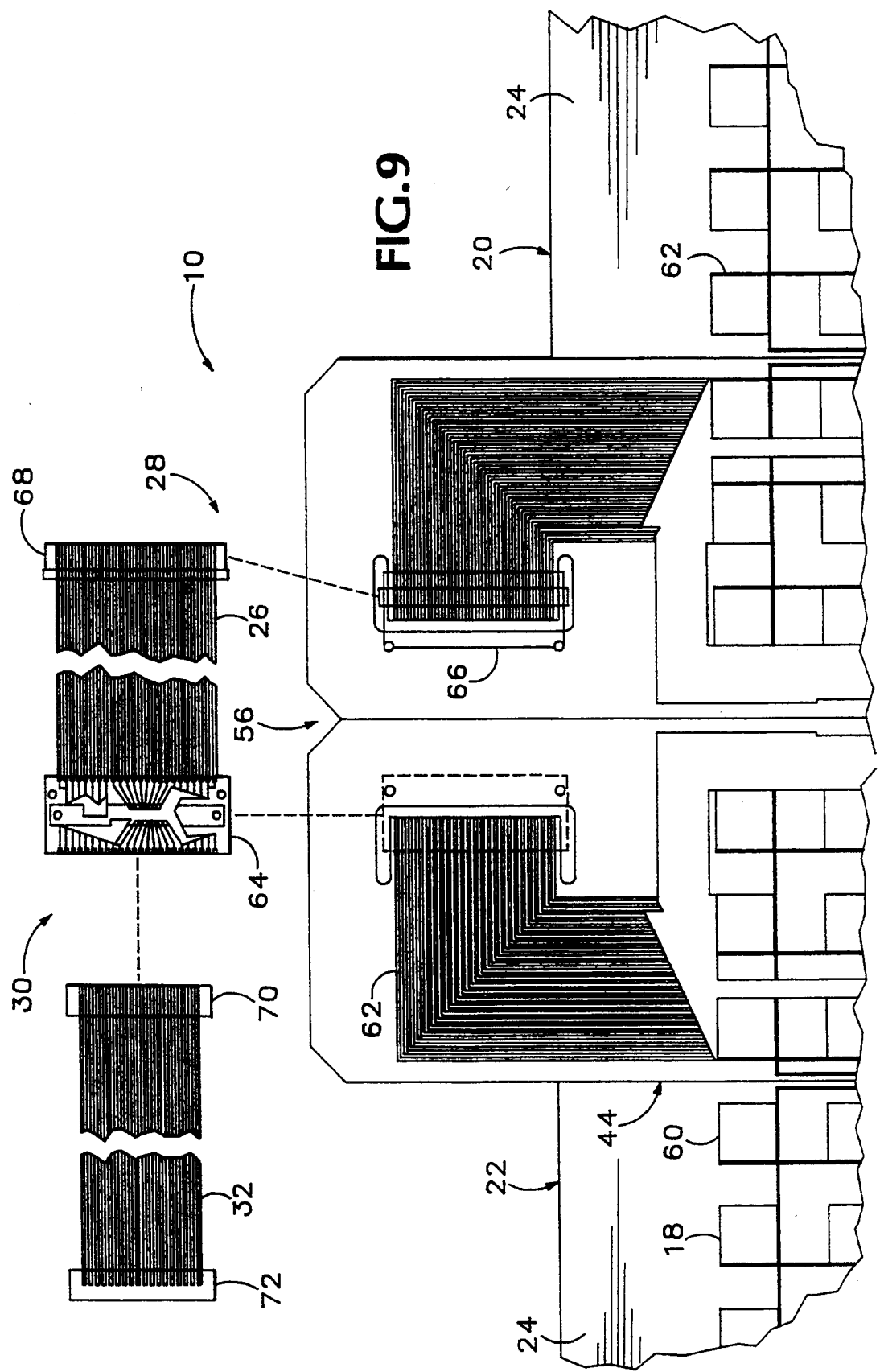
FIG. 9 is an assembly including a further enlarged fragmentary view of the pad of FIG. 7 with connector cables.

FIG. 9 shows the general structure of the connections made to the pad for coupling the output of the various sensors to a computer. By positioning the terminations of the conductor traces to be aligned in parallel, they are readily connected by service loop 26 in the form of a flex cable. The service loop conveys signals from an 8×16 matrix which requires that it have at least 24 conductors. A conventional 25-conductor cable is therefore suitable for this purpose. Service loop 26 is terminated with a receptacle 68 for connection to pin housing 66, which receptacle and housing form connector assembly 28. The other end of loop 26 is connected to the circuit board, as shown particularly in FIG. 9.

The ends of ribbon cable 32 are connected to male connectors 70 and 72. Connector 70 connects to a vertical mount receptacle 74 connected at its base to a circuit board 64, all forming connector assembly 30. Connector 72 is connectable to a conventional computer 76 as is illustrated in FIG. 9. Cable 32 services the entire 16×16 composite array, and therefore must have at least 32 conductors. A conventional 36-conductor cable is therefore adequate.

Circuit board 64 is powered by a resident battery or other power supply, not shown. It provides for converting the analog sensor signals into digital signals, and multiplexes the array signals for transmission over cable 32 in a predetermined sequence. Computer 76 is then programmed to receive this data and generate suitable output reports and displays.

If it is desired to position the computer near a horse during testing, cable 32 can be gathered in an accordion fashion over service loop 26 and retained releasably, such as by rubber bands extending across posts mounted on tongues 42a, or otherwise as is desired. If the horse moves suddenly, then the cable releases, avoiding movement of the computer and stress on the cable connections.

Figure 11:
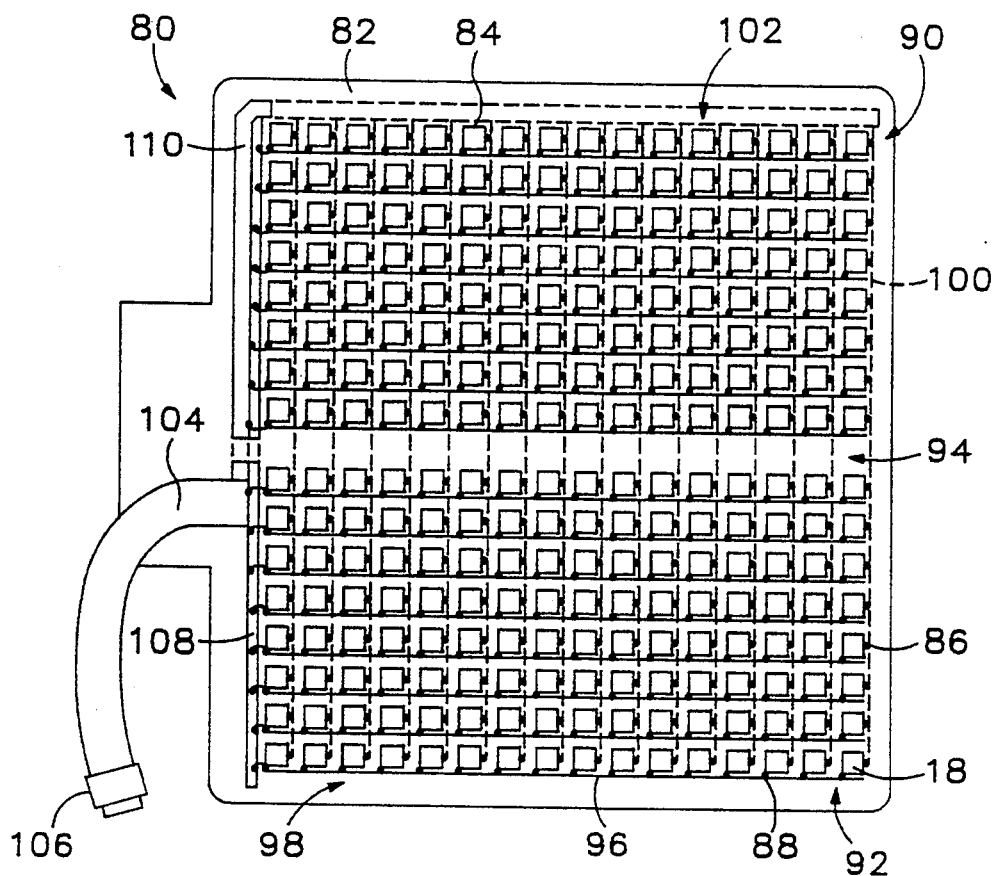
FIG. 11 is a plan view of an alternative embodiment of the pad of FIG. 1.
Figure 12:
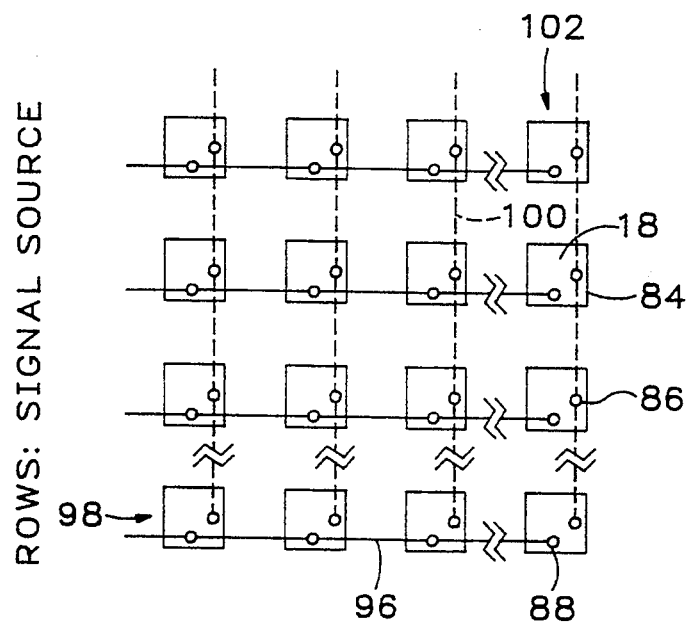
FIG. 12 is a schematic illustrating the layout and wiring of the array in the pad of FIG. 11.

FIG. 11 illustrates a second preferred array pad 80. Pad 80 includes a continuous composite membrane 82 formed of a flexible, stretchable material, such as that commonly known by the proprietary name Lycra. Individual sensors 18, that are substantially the same as those described with reference to pad 14, are imprinted on individual membrane pieces 84. The membrane pieces are made of the same material as membrane 24 and are attached to membrane 82 by grommets 86 and 88 and a suitable bonding agent. Membrane 82 thus allows movement between adjacent edges of the nonstretchable membrane pieces, which may also be considered in a general sense to be sections of the membrane.

Pad 80 includes two arrays 90 and 92 of sensors 18. Arrays 90 and 92 are spaced apart by a connecting section 94 of the membrane. It has been found that due to the downward angle of a saddle on a horse's back, shear forces are applied by a saddle on the back of a horse. When a sensor array pad is placed between the horse and saddle, these shear forces are applied to the sensors. The pressure readings are thereby distorted by the shear forces.

When the planar sensors are carefully placed between opposing planar surfaces of the horse and saddle without wrinkles in the membrane, the amount of shear is reduced. The shear forces are further reduced by manually gathering connecting membrane section 94 so that it is in a slack or relaxed state. During riding, the pad arrays tend to creep downward due to the shear forces. This movement of the arrays is allowed by take-up of the connecting section without a corresponding increase in the shear forces. The shear forces are greatest when the central section is pulled tight.

Gathering of the connecting section pulls the arrays up slightly. This seats the sensors better between the horse and saddle, improving contact between the sensors and the saddle. These actions, which can also be performed on pad 14, reduce erroneous signal components and thereby make the sensed signals more accurate. By not having sensors in the connecting section, the membrane can be manually rearranged without concern for damaging the array of sensors.

A 16-conductor braided cable 96 extends along the length of each row 98 of sensors in the composite of arrays 90 and 92. Each cable 96 is connected to the 16 sensors in the row by corresponding grommets 88. These cables provide an output signal to the sensors. The cable is pushed into itself during installation to allow the cable to, in effect, stretch during use in response to stretching of membrane 82 between adjacent relatively rigid sensor membrane pieces 84.

Similarly, the data is returned to the computer via laterally extending cables, such as cable 100. Cables 100 are connected to respective sensors 18 forming a column 102 by associated grommets 86. These return cables are mounted on the underside of membrane 82 in order to not interfere with longitudinal cables 96. Individual cables 96 and 100 are connected to a 32-conductor ribbon cable 104 and interface connector 106 via respective feeder cables 108 and 110 fastened along the margins of the membrane, as shown.

Figure 13:
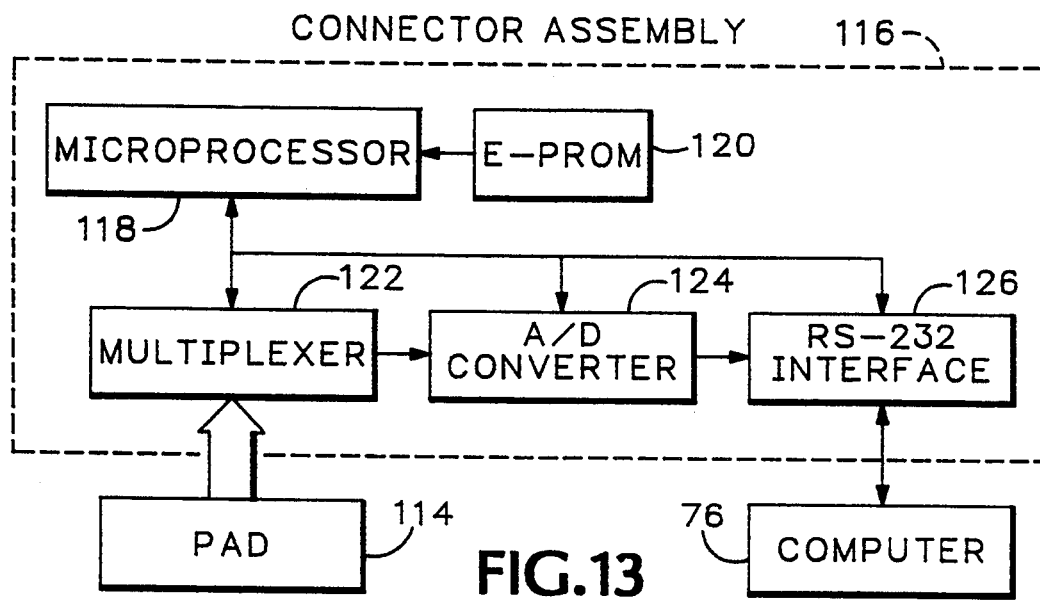
FIG. 13 is a block diagram of a computerized system for practicing the method of the invention.

FIG. 13 is a block diagram of a computerized system 112 for practicing the method of the present invention. System 112 utilizes a pad assembly made with either pad 14 or pad 80 for providing the distributed array of pressure-responsive sensors 18. The pad is preferably enclosed in a plastic covering or envelope (not shown) to protect the sensors during use. Except for the design and configuration of these pads, this system is very similar to those used for measuring the pressures on a patient supported for extended periods of time on a wheel chair or bed.

Figure 10:
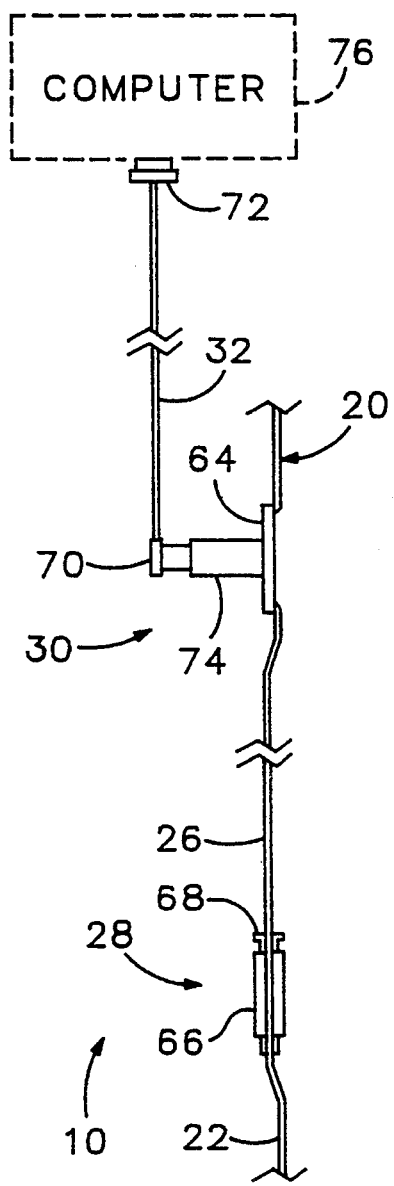
FIG. 10 is a side view of the assembly of FIG. 9.

System 112 includes a sensor array pad 114 connected to a connector assembly 116, corresponding to connector assembly 30 and in particular to circuit board 64 shown in FIG. 10, and computer 76, such as a conventional personal computer. The connector assembly electronics include a microprocessor 118 and an E-PROM (erasable programmable ROM) 120 which stores a program and operating data. The microprocessor controls operation of a multiplexer 122, an analog-to-digital converter 124, and an RS-232 computer interface 126.

Figure 14:
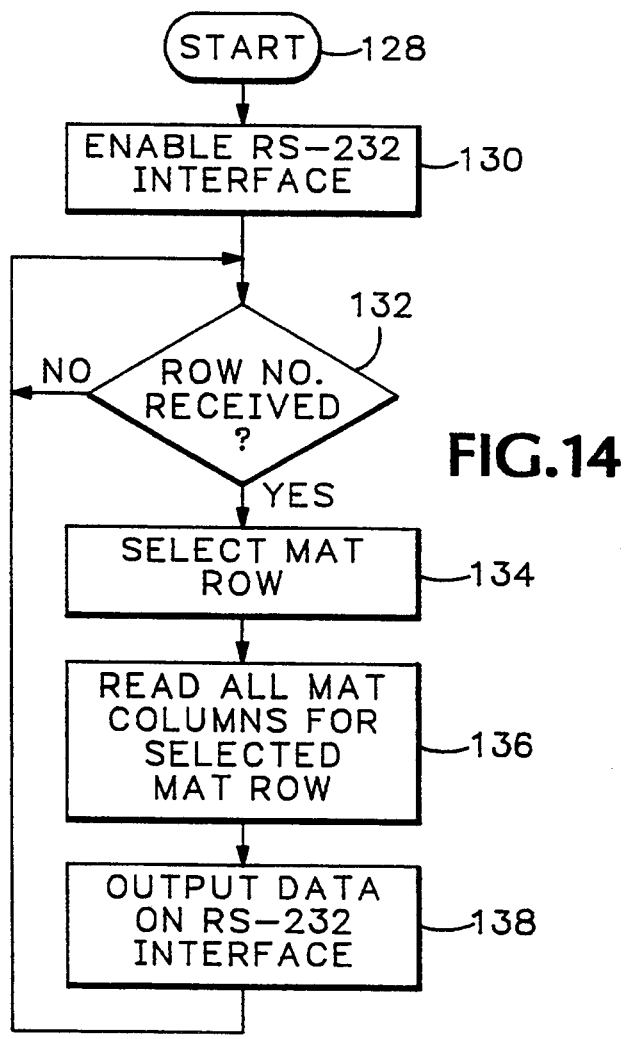
FIG. 14 is a flow chart of the operation of the pad/computer connector assembly of FIG. 13.

As shown in FIG. 14, when operation of connector assembly 116 is started at power up, as represented by step 128, the RS-232 interface with a computer 76 is enabled at step 130 and the multiplexer is initialized in a "wait for instruction" mode. During this waiting period continuous inquiry is made at decision step 132 as to whether a selected row number is received from the host computer. When a row number is received, the multiplexer selects that row in the array of pad 114 at step 134, and scans each column input line with the selected row output line activated.

Upon reading of the sensor data for the columns at step 136, the sensed analog pressure signals in the form of current are converted into digital format by A/D converter 124. The data is then amplified and sent serially to computer 76 out of the RS-232 port, as shown by step 138.

Figure 15:
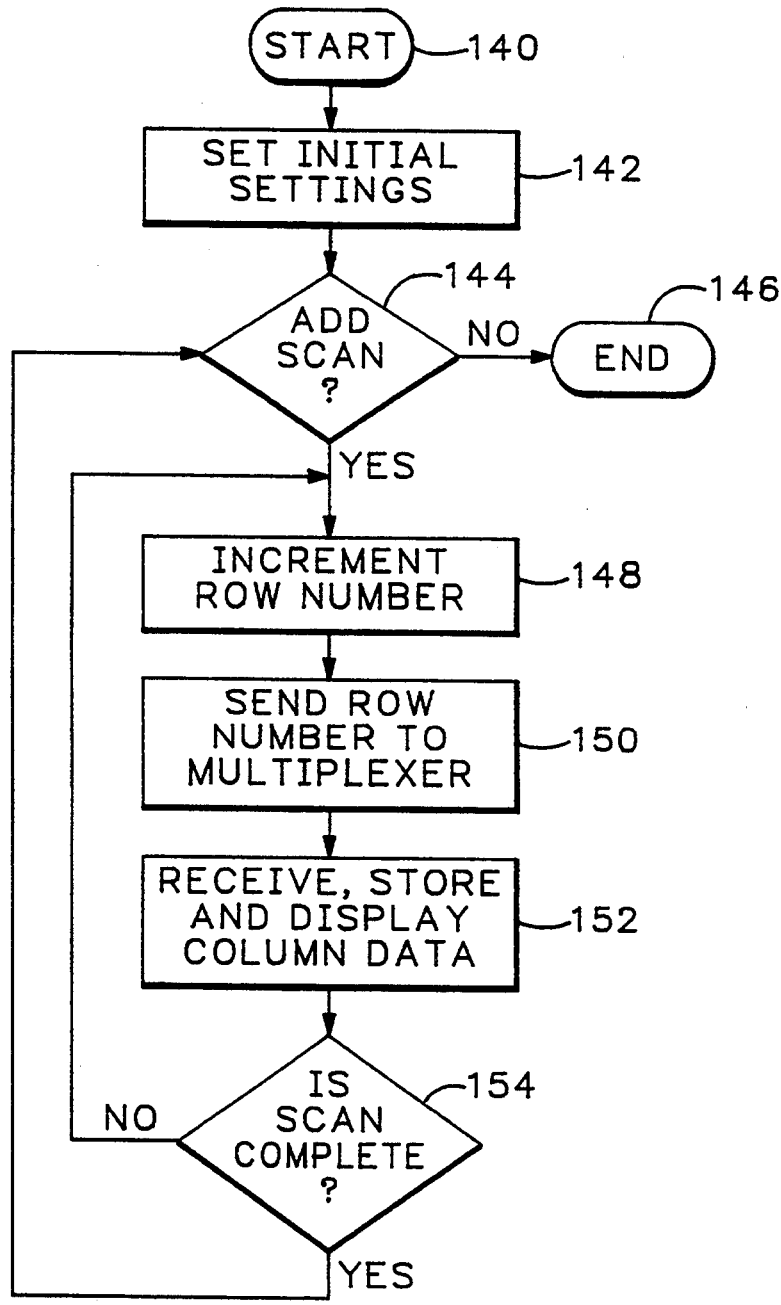
FIG. 15 is a flow chart of the computer operation for generating a display of a saddle-pressure-distribution sensed by the pad of FIGS. 1, 5 or 11.

Operation of computer 76 is illustrated in FIG. 15. After power up of the computer as shown by start step 140 the program variables are given initial settings at step 142. A query at step 144 is made as to whether a scan is being added. A scan is added when a user inputs a command to start a new scan. If no scan is to be added the program ends this portion of the program operation at step 146. Other features, not part of the present invention, allow for the recall from memory of an individual scan or a plurality of scans for display on a monitor or on hard copy.

When a command for a new scan is received, the row number from an initialized value is incremented to the first row of a scan at step 148 and the row number is sent at step 150 to multiplexer 122 via RS-232 interface 126 in connector assembly 116 for scanning as has been described with reference to FIG. 14. The scanned column data for the selected row is then received from the multiplexer, converted to pressure readings, stored in memory, and displayed, all represented by step 152.

A query is then made at decision step 154 as to whether the scan is complete. It is complete when all of the rows have been scanned. If the scan is incomplete, then processing is returned to step 148 which increments the row number and new scan data is obtained following steps 150 and 152. If the scan is complete, then processing is returned to step 144 to determine if the user desires to generate another Scan.

Figure 16:
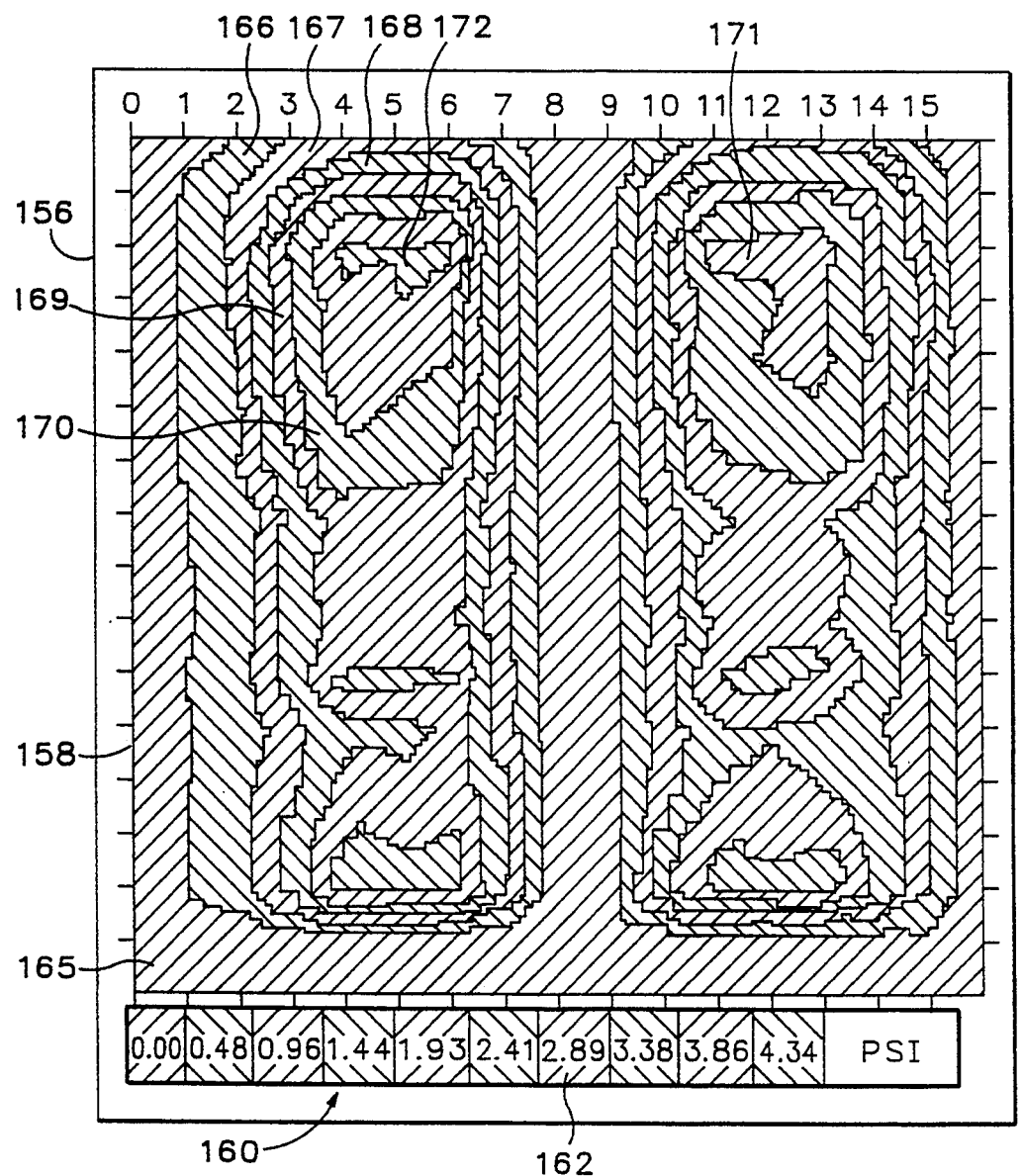
FIG. 16 is a monitor graphic display of a pressure distribution generated with the computer of FIG. 13.

Various forms of displaying the scan data are possible. A matrix array or tabulation of pressure values may be printed out or shown on a monitor. A more easily understood format though is the mapping of the sensed pressures on an image of the pad array using different colors to represent different pressures or pressure ranges. FIG. 16 illustrates such a display 156. This display includes an image 158 of the 16×16 composite sensor pad array formed of two spaced-apart arrays as shown. The correspondence between pressures and colors, here shown as shades of gray, is provided by the legend 160 which displays an associated pressure over a patch 162 of the associated color. Since the pressures typically vary continuously through a range of pressures in the image, the areas of high pressure are immediately recognizable.

In the image shown, the pressures vary from no pressure represented by areas 164 to pressure areas according to the pattern produced by a saddle. The pressure levels illustrated increase from none to 3.38 psi, in increments of 0.48 psi. These areas of increasing pressure levels are represented respectively by areas 165–172, corresponding to pressures from 0.48 psi to 3.38 psi. These values correspond to a range of pressure readings between 0 and 4 psi. Similar displays may be selected for pressures ranging between 0 and 1 psi and between 0 and 2 psi, displayed respectively in increments of 0.11 psi and 0.24 psi.

When it is determined that an excessive pressure exists, the situation is cured by changing the distribution of pressures. If the excessive pressures are redistributed over a broader area, the high pressures will be reduced, and correspondingly the pressure in lower pressure areas will increase. This adjustment in the pressure distribution may be accomplished in several ways. If the user is not limited to the existing saddle on the horse, a saddle with a different structure may be substituted. The pressure distribution is then rescanned as discussed with reference to FIGS. 14 and 15 in order to determine if the pressure distribution is more favorable.

If the user is limited to a single saddle, then the pressure distribution must be accommodated by changing structure associated with that saddle. It would be expensive to disassemble and rebuild the saddle. One alternative is to use one or more of various commonly available air, sheepskin, and foam saddle pads.

Another alternative, particularly for those saddles having a fabric cover on the panel facing the horse, is to adjust the position of the flocking in the panel. This flocking provides cushioning between the hard structure or tree of the saddle and the horse. By sticking a pointed instrument, such as an ice pick, through the cover and into the flocking and moving it so that the thickness of the flocking is reduced in the area of the high pressures, the amount of force transmitted through that area is reduced. Repeated scans of the pressure distribution provide the necessary feedback to determine the effectiveness of the redistribution of the flocking.

This technique requires the user to be able to relate the pressure display to the areas of the surface of a saddle that has been removed and turned upside down. This is facilitated by a template (not shown) made with a clear plastic sheet that has the image of the sensor arrays printed on it, as shown in FIG. 11. The rows and columns are identified on this template the same as they are represented on the display screen as shown in FIG. 16. This template is then placed to conform with the bottom surface of the saddle. A point on the display is then readily located on the saddle.

The distribution of pressure between the saddle and horse is also affected by the position or posture of the rider. Different postures produce different pressure distributions. Thus, the pressure in high pressure areas may be reduced by having the rider adjust her or his posture. Balanced equitation is an important part of developing the most favorable weight distribution and overall interaction between horse and rider. With experience, the pressure distribution pattern provides additional feedback on how well the rider is balanced. For such uses it is important that the pressure sensing occur while the rider is actively riding the horse.

The preferred embodiments of the invention are manufactured at low cost. Most conventional sensor arrays as well as the embodiment of FIG. 11 are comprised of individual sensors that are manually attached and wired to a flexible membrane. Such arrays are more expensive to manufacture than the silkscreen process of the embodiment of FIGS. 1–9. Further, the present invention provides a sensor pad that is very thin, thereby minimizing the interference with the fit between a conventional saddle and a horse. Further, the formation of a non-stretchable membrane with selective slits that conform to the sensor array and conductor traces that conform to the slits, allows a simple pad to conform to a compound curvature surface without wrinkles.

The use of a continuous stretchable membrane however allows for accommodation of a change in curvature of the back of a horse between adjacent sections of the pad occupied by individual sensors. This distributes the distortion of the pad over a wider area. The present method of measuring the distribution of pressure between a saddle and the back of a horse provides information on saddle fit and rider:balance. More even pressure distribution increases the comfort for the horse, thereby reducing soreness and improving performance.

It will be apparent to one skilled in the art then, that variations in form and detail may be made in the preferred embodiments and methods without varying from the spirit and scope of the invention as defined by the claims and by any modification of the claim language or meaning as provided under the doctrine of equivalents. The preferred embodiment is thus provided for purposes of explanation and illustration, but not limitation.

I claim:

1. A sensor array pad for sensing the pressure distribution under a saddle on the back of a horse comprising:
 a plurality of generally planar sensors each having a planar surface and associated edges, each sensor being responsive to a pressure applied on the planar surface for outputting a signal representative of the applied pressure; and
 means for supporting said plurality of sensors in a pair of arrays, with each array distributed over an area corresponding to at least a portion of the area of a saddle that is supported on one side of the spine of a horse with one of said arrays positionable on each side of the spine of a horse and the planar surfaces of the respective sensors conforming to the compound curvature of a horse's back when said pad is placed between a saddle and a horse's back.

2. A sensor array pad according to claim 1 wherein said supporting means comprises, for each array, a stretchable, flexible membrane extending over at least a portion of said area and means for mounting said sensors relative to said membrane.

3. A sensor array pad according to claim 2 wherein said membrane covers an area of a horse's back corresponding to a known type of saddle.

4. A sensor array pad according to claim 2 wherein said membrane is continuous over said area and said mounting means mounts said sensors at spaced positions on said membrane.

5. A sensor array pad according to claim 2 wherein said supporting means further comprises, for each array, a plurality of sections of a substantially non-stretchable, flexible membrane with said sections having adjacent separate edges joined by said stretchable, flexible membrane.

6. A sensor array pad according to claim 1 wherein said supporting means supports said plurality of sensors in each of said arrays in a plurality of sections having respective adjacent edges, and further accommodates a change in curvature of the array when supported on the back of a horse by allowing at least a portion of the adjacent edges of a portion of said sections to move relative to each other.

7. A sensor array pad according to claim 6 wherein each of said sections comprises a continuous membrane, said supporting means further comprising means for resiliently urging together separated portions of the respective adjacent edges of said sections allowed to move relative to each other.

8. A sensor array pad according to claim 6 wherein each of said sections comprises a continuous membrane, with at least two of said sections being disconnected along at least a portion of the respective adjacent edges, whereby the sections, when supported on the back of a horse, are allowed to separate along the disconnected adjacent edges and conform to the back of the horse.

9. A sensor array pad according to claim 8 wherein said membrane is substantially non-stretchable and flexible, and lies flat when placed on a planar surface.

10. A sensor array pad according to claim 9 wherein said supporting means further comprises means for holding at least a portion of an adjacent edge of each section in a fixed position with respect to the respective adjacent edge of an adjacent section whereby the plurality of sections are held adjacent to each other when supported on the back of a horse.

11. A sensor array pad according to claim 10 wherein said holding means comprises a joining section of membrane that is integral with the respective adjacent edges of at least two adjacent sections for combining at least a portion of said sections as a continuous single membrane.

12. A sensor array pad according to claim 10 wherein the respective disconnected adjacent edges terminate in an enlarged opening.

13. A sensor array pad according to claim 10 where the back of a horse has an upper portion that is concave as viewed from the side and a side portion that is convex as viewed from the head, and wherein said supporting means includes first and second adjacent sections adapted to conform to the upper portion and the side portion respectively when said pad is placed on the back of a horse.

14. A sensor array pad according to claim 13 wherein said supporting means further includes third and fourth sections with the first section attached to each of said second, third, and fourth sections, with said second and third sections and said third and fourth sections, respectively, having disconnected adjacent edges, with said first, second, third and fourth sections conforming to the curvature of a horse's back when said first section is positioned adjacent to the spine of a horse's back with said second, third and fourth sections supported pendently from said first section.

15. A sensor array pad according to claim 14 further comprising four additional sections forming a mirror image of said first, second, third, and fourth sections with said first section and the corresponding one of said four additional sections being joined together at spaced-apart locations.

16. A sensor array pad according to claim 15 wherein said first and corresponding sections have respective adjacent edges that are spaced apart between the spaced-apart locations.

17. A sensor array pad according to claim 1 wherein said supporting means includes a non-stretchable membrane supporting each of said arrays of sensors, said membrane having adjacent edges, and said supporting means further includes means for holding said adjacent edges of said membrane at two spaced-apart locations corresponding to positions along the spine of a horse when said pad is placed on the back of a horse.

18. A sensor array pad according to claim 17 wherein said adjacent edges between said two-spaced-apart locations form an open slit when said pad is placed on a planar surface.

19. A sensor array pad according to claim 17 wherein said holding means comprises tabs extending from each adjacent edge of said membranes and means for adhering the tabs together.

20. A sensor array pad according to claim 1 wherein said supporting means supports said sensors in two spaced-apart arrays, whereby a central portion corresponding to the spine of a horse is without sensors.

21. A sensor array pad for sensing the pressure distribution under a saddle on the back of a horse comprising:
a membrane formed of first and second substantially non-stretchable, flexible membrane portions for positioning on the back of a horse, said first and second membrane portions being formed identically and having adjacent edges that are joined at two spaced-apart locations, said joined membrane portions lying flat on a planar surface and being sized to support a saddle on the back of a horse with said adjacent edges extending along the spine;
a plurality of sensors distributed substantially uniformly on said first and second membrane portions, with each sensor occupying a predetermined surface area; and
conductors mounted on said membrane extending between said sensors and a position along a perimeter of the associated membrane portions;
said first and second membrane portions further each having a pair of slits extending from a mid-region spaced from said associated adjacent edge outwardly in diverging directions along lines passing outside the predetermined areas of the membrane occupied by said sensors, the slits defining an upper section for extending generally alongside the spine of a horse and a side section extending down the side of the horse away from the spine, whereby said membrane portions, when placed on the back of a horse with said adjacent edges extending along the spine, generally conform to the back of the horse with said upper and side sections separating along the slits.

22. A method for sensing the pressure under a saddle on the back of a horse comprising the steps of:

positioning between a saddle and the back of a horse a pad having at least one individual pressure-responsive sensor in a fixed position of the pad;

positioning a rider in the saddle;

sensing from the at least one sensor a signal representative of the pressure applied by the saddle; and determining from the sensed signal the pressure represented by the signal.

23. A method according to claim 22 further comprising the step of producing a visual display of the determined pressure.

24. A method according to claim 22 wherein said method further comprises the steps of changing the distribution of pressure applied by the saddle on the horse, sensing from the at least one sensor a modified signal representative of the pressure applied by the saddle on the horse, and determining from the modified sensed signal the pressure represented by the modified signal.

25. A method according to claim 24 wherein said step of changing comprises changing the structure of the saddle on the horse.

26. A method according to claim 25 wherein said step of changing the structure comprises adjusting the position of padding between the saddle and the horse.

27. A method according to claim 25 wherein said step of changing includes replacing the saddle with a different saddle having a different structure.

28. A method according to claim 24 wherein said step of changing comprises changing the position of the rider in the saddle.

29. A method according to claim 28 further comprising the step of riding the horse during said steps of sensing and determining.

30. A method according to claim 22 wherein said step of positioning the at least one sensor includes positioning the pad with an array of individual pressure-responsive sensors distributed over an area corresponding to the area of at least a portion of the saddle on the back of the horse, the step of sensing includes sensing the pressure-representative signal from each sensor, and said step of determining includes determining the pressure represented by each sensed signal.

31. A method according to claim 30 further comprising the step of producing a visual display of the determined pressures sensed by each sensor.

32. A method according to claim 31 wherein said step of producing includes producing a two-dimensional graphic display representative of the determined pressures in relative positions corresponding to the relative positions of the associated sensors in the array.

* * * * *

REEXAMINATION CERTIFICATE (3670th)

United States Patent [19]
Ferrand et al.

[11] B1 5,375,397
[45] Certificate Issued  Nov. 10, 1998

[54] CURVE-CONFORMING SENSOR ARRAY PAD AND METHOD OF MEASURING SADDLE PRESSURES ON A HORSE

[76] Inventors: Robert J. Ferrand, 121 Bancroft Rd., Burlingame, Calif. 94010; Joseph A. Sember, III, 2339 Paseo De Cima, Glendale, Calif. 91206

Reexamination Request:
No. 90/004,349, Aug. 30, 1996

Reexamination Certificate for:
Patent No.: 5,375,397
Issued: Dec. 27, 1994
Appl. No.: 196,984
Filed: Feb. 15, 1994

Related U.S. Application Data

[63] Continuation-in-part of Ser. No. 80,805, Jun. 22, 1993, abandoned.

[51] Int. Cl.$^6$ ........................................................ B68C 1/12
[52] U.S. Cl. ........................................................ 54/66; 600/595
[58] Field of Search ........................... 54/65, 66; 128/782

[56] References Cited

U.S. PATENT DOCUMENTS

| | | | |
|---|---|---|---|
| 809,276 | 1/1906 | Aulton | 54/65 |
| 823,590 | 6/1906 | Eichorn | 54/66 |
| 1,357,823 | 11/1920 | Read | 54/66 X |
| 3,543,724 | 12/1970 | Kirkpatrick et al. | |
| 3,872,653 | 3/1975 | Thompson | 54/66 X |
| 4,014,398 | 3/1977 | Gresko | 128/782 X |
| 4,478,225 | 10/1984 | Ewing | |
| 4,935,887 | 6/1990 | Abdalah et al. | 364/578 |
| 4,957,286 | 9/1990 | Persons, II et al. | 73/379 X |
| 4,957,444 | 9/1990 | Armen | 434/247 |
| 4,988,300 | 1/1991 | Yamaguchi et al. | 434/247 |
| 5,010,772 | 4/1991 | Bourland et al. | 73/862.04 |
| 5,119,618 | 6/1992 | Streck | 54/66 |
| 5,253,656 | 10/1993 | Rincoe et al. | 128/782 |
| 5,369,601 | 11/1994 | Tannenbaum | 364/558 |

OTHER PUBLICATIONS

Nicol, Letter to P. Seitz, Apr. 22, 1995.
Heipertz-Hengst, Electronic Timed Pressure Distribution In Riding Posture With Synchronic High-Frequency Film Analysis, 1981.
Heipertz-Hengst, Biomechanics of Riding, 1982.
Heipertz-Hengst, Wirkungen des Therapeutischen Reitens, 1984.
Blümcke, Reiten Wird Elektronigek Messbar, Jun. 1989.
Biomechanics IX-A, 1983.
EMED-System Technical Applications Brochure, Dec. 1992.
FDA Finding Letter, May 1993.
Van Amerongen, The Way Things Work, 1971, pp. 296–297.
Koff, How Does It Work, 1961, pp. 127–131.

*Primary Examiner*—Robert P. Swiatek

[57] ABSTRACT

A sensor array pad for sensing the pressure distribution under a saddle on the back of a horse includes a membrane made of first and second, identical substantially non-stretchable, flexible membrane portions. The membrane portions have adjacent facing edges that are joined at two spaced-apart tabs. A plurality of sensors are distributed substantially uniformly on the membrane, with each sensor occupying a predetermined surface area. Conductors are mounted on the membrane to extend between the sensors and a position along the perimeter of the associated membrane portion to provide for external connection with monitoring equipment. The membrane portions further each have a pair of slits extending from a mid-region spaced from the respective facing edge outwardly in diverging directions along lines passing outside the predetermined areas of the membrane occupied by the sensors. The slits define an upper section extending generally along the spine of a horse and a side section extending down the side of the horse away from the spine. When placed on the back of a horse with the facing edges extending along the spine, the membrane generally conforms to the back of the horse with the upper and side sections separating by spreading of the slits. The membrane may also be stretchable between the individual sensors. Pressures sensed by the sensors are input to a computer which generates a display of the pressure distribution.

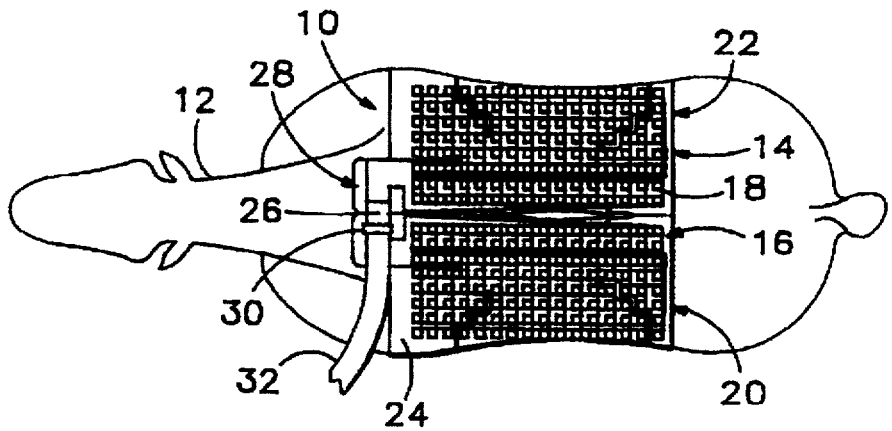

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 5–16 and 21 is confirmed.

Claims 1–4, 17–20, 22–31 and 32 are cancelled.

* * * * *